United States Patent

Feijen et al.

Patent Number: 5,496,557
Date of Patent: Mar. 5, 1996

[54] ARTICLE FOR THE CONTROLLED DELIVERY OF AN ACTIVE SUBSTANCE, COMPRISING A HOLLOW SPACE FULLY ENCLOSED BY A WALL AND FILLED IN FULL OR IN PART WITH ONE OR MORE ACTIVE SUBSTANCES

[75] Inventors: Jan Feijen, Hengelo; Hilbert Esselbrugge, Enschede, both of Netherlands

[73] Assignee: Akzo N.V., Ls Arnhem, Netherlands

[21] Appl. No.: 917,058

[22] PCT Filed: Jan. 30, 1991

[86] PCT No.: PCT/NL91/00013

§ 371 Date: Aug. 24, 1993

§ 102(e) Date: Aug. 24, 1993

[87] PCT Pub. No.: WO91/11176

PCT Pub. Date: Aug. 8, 1991

[30] Foreign Application Priority Data

Jan. 30, 1990 [NL] Netherlands ............................ 9000221

[51] Int. Cl.$^6$ .................................................. A61F 2/00
[52] U.S. Cl. .................... 424/426; 424/428; 424/438; 424/490; 424/491; 424/497
[58] Field of Search ................................. 424/490, 426, 424/438

[56] References Cited

U.S. PATENT DOCUMENTS 4,994,279  2/1991  Aoki ........................................ 424/494

FOREIGN PATENT DOCUMENTS

| 0153825 | 9/1985 | European Pat. Off. . |
| 0168862 | 1/1986 | European Pat. Off. . |
| 0243263 | 10/1987 | European Pat. Off. . |
| 2216411 | 10/1989 | United Kingdom . |
| 9105574 | 2/1992 | WIPO . |

*Primary Examiner*—D. Gabrielle Phelan
*Attorney, Agent, or Firm*—Mary E. Gormley

[57] ABSTRACT

An article for the controlled delivery of an active substance, comprising a hollow space fully enclosed by a wall and filled in full or in part with one or more active substances, which wall is made using a biodegradable polymeric material permeable to the active substance, wherein the wall is composed mainly of a combination of at least two different polymeric materials in which one polymeric material is permeable to the active substance and is degradable and the other polymeric material is relatively poorly permeable to the active substance and is degradable and the conveyor path for the delivery of the active substance from the hollow space to the surroundings of the article is a continuous distance leading at least through the polymeric material permeable to the active substance.

19 Claims, 1 Drawing Sheet

ARTICLE FOR THE CONTROLLED DELIVERY OF AN ACTIVE SUBSTANCE, COMPRISING A HOLLOW SPACE FULLY ENCLOSED BY A WALL AND FILLED IN FULL OR IN PART WITH ONE OR MORE ACTIVE SUBSTANCES

BACKGROUND OF THE INVENTION

This invention relates to an article for the controlled delivery of an active substance, comprising a hollow space fully enclosed by a wall and filled in full or in part with one or more active substances, said wall being made using a biodegradable polymeric material permeable to the active substance.

For the controlled delivery of active substances articles have been developed showing a great diversity in shape, sizes and other properties capable of affecting the rate of delivery of an active substance from the usability of the article. Particularly the selection of the material of which the article is made can largely affect the final possibilities of using the article. On the basis of the nature of the materials used, which are often polymeric materials, it is possible to divide the articles for the controlled delivery, which, among other things, are intended for use in man and animal, into two groups. On the one hand, there are the articles made of materials that cannot be broken down in the body. After the active substance has been delivered, the article must be removed, which may be regarded as a drawback. On the other hand, there are the articles on the basis of (bio) degradable materials. When the active substance has been delivered in full or in part, a breakdown of the article into components innocuous to the organism occurs so that removal of the article is no longer necessary.

"Hydrogels and Biodegradable Polymers for the Controlled Delivery of Drugs" by N. B. Graham and D. A. Wood in Polymer News, 1982, Vol. 8, pages 230–236, discloses all kinds of delivery systems of the basis of biodegradable polymer substrates charged with active substance, which polymer substrates, among other things, can be subdermally applied to man and animal. Such delivery systems may have the form of e.g., spherical particles. These particles consist of biodegradable matrices surrounding the active substance. Such a delivery system, however, has the drawback that the particles can hardly, if at all, be surgically removed should the active substance would not be accepted. The same drawback is connected with other delivery systems referred to in this article, such as microcapsules having an average size of 5 to 50 µm. The above article by N. B. Graham and D. A. Wood further mentions films as delivery system. Such films, however, have the drawback that a subdermal use thereof requires surgery, which is considered laborious and may also involve certain risks.

The usability of an article is not exclusively determined by the possibility of breakdown of the article after delivery of the active substance. Also the possibilities of a proper control of the rate of delivery of the active substance are important when designing an article. Because in many cases the active substance will be released by a diffusion process, the material selection may again be a decisive factor for the delivery properties finally obtained by the article. Besides, it is also possible to affect the delivery properties by varying the shape and sizes of the article.

"Sustained Drug Delivery System II: Factors Affecting Release Rates from poly-ε-caprolactone and Related Biodegradable Polyesters" by C. G. Pitt et al in J. Pharm. Sc., Vol. 68, No. 12, 1979, pages 1534–1538, discloses films on the basis of homo—and copolymers of ε-caprolactone, DL-lactic acid and glycolic acid. With regard to the microcapsules on the basis of poly-ε-caprolactone described in this article and in U.S. Pat. No. 4,148,871 of C. G. Pitt et al (1986) it is particularly advanced that these are prepared by melt extrusion, after which the ends of the resulting hollow tube are closed after filling with the medicine. These microcapsules, however, have the drawback that the rate of delivery of the medicine per unit of area, which is adjustable by varying the wall thickness of the hollow tube, can only be changed to a very limited extent, e.g., by a factor of 2 to 3.

For the delivery of active substances having a high molecular weight, European Patent Application No. 86402527.5 (Porous bioadsorbable polyesters, 1986) of A. Schindler describes the development of a porous degradable fibre made of polymer.

"Controlled Release Technologies: Methods, Theory and Applications" Vol II by A. F. Kydonieus, page 165 ff , CRC Press, Inc., discloses the use of hollow fibers for the delivery of insect pheromones. Further, "Hollow Fibers as an Oral Sustained-Release Delivery System" by M. A. Hussain et al in Pharm. Res., Vol. 6, No. 1, 1989, pages 49–52, describes the delivery of Phenyl Propanolamine (PPA) from hollow fibers. As indicated, however, such hollow fibers are open on one side so that they are unsuitable for the controlled delivery of medicines in a subdermal or other use in man and animal.

BRIEF DESCRIPTION OF THE INVENTION

The object of this invention is to obtain an improved article for the controlled delivery of an active substance which does not have the above drawbacks.

According to this invention an article of the type referred to in the opening paragraph is provided which is characterized in that the wall is composed mainly of a combination of at least two different polymeric materials in which one polymeric material is permeable to the active substance and is degradable and the other polymeric material is relatively poorly permeable to the active substance and is degradable and the conveyor path for the delivery of the active substance from the hollow space to the surroundings of the article is a continuous distance leading at least through the polymeric material permeable to the active substance.

DETAILED DESCRIPTION OF THE INVENTION

Figure 1A:
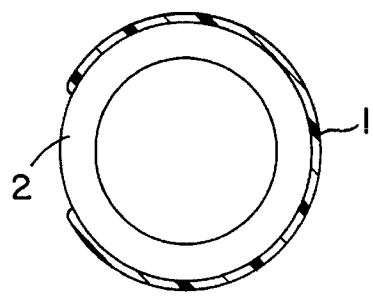
FIGS. 1a and 1b show how a polymeric layer poorly permeable to the active substance partially covers the interior or exterior of the highly permeable layer.

The article according to this invention is a hollow article made of a combination of biodegradable polymers, in which article the hollow space may contain a pure active substance, a dilute form or a dispersion of this substance in a matrix and the ends, edges etc. of the article are closed.

The biodegradable polymers to be used for the hollow article may be polyesters such as polylactic acid, polyglycolic acid, poly (ε-caprolactone), poly(β-hydroxybutyric acid), poly (hydroxyvalerate), poly(orthoesters), poly(α-amino acids), including esters of polyglutamic acid and finally polydepsipeptides, polyanhydrides and polyphosphazenes. Moreover, all the (co)polymers derived from the above polymers may be used, including block copolymers and stereo complexes of polymers formed from optically active monomers from the above groups.

When the article according to this invention is used subdermally, use is preferably made of (co)polymers that are properly degradable and do not give body-foreign products and/or toxic by-products after or during degradation. Examples thereof are polylactic acid, poly(β-hydroxybutyric acid), poly (ε-caprolactone), poly(α-amino acids) as well as derived (co)polymers.

The hollow articles used may have such shapes and such sizes that in human use they can be applied subdermally without problems in accordance with generally accepted guidelines. Consequently, the articles made according to this invention may be injectable so that a surgery need not take place. Because the articles according to the invention preferably have a length up to 5 cm, they can be easily traced. When used veterinarily, the sizes of the article may be considerably larger.

In the hollow space of the articles various active substances can be used, such as medicines, hormones and related products. When inserted, the articles according to the invention deliver the active substance to the body for a certain period of time which may vary, e.g., from 1 week to some years. According to this invention the delivery period and the delivery rate of the active substance used can be easily adjusted by adaptation to the structure of the article.

The biodegradable article according to this invention charged with active substance can be used in agriculture and horticulture, in which insecticides, pheromones, repellents, and related products may be used as the active substances.

The hollow articles used according to this invention consist of a combination of two or more polymeric materials having different permeabilities to the active substance. For the purpose of illustration a combination of two polymers will be described hereinbelow. Moreover, by way of example in this specification, the article for the controlled delivery will have the form of a hollow tube. Thus starting from a combination of two polymers, a first polymer will have to show a relatively high permeability to the active substance, while the second polymer has a relatively low to very low permeability to the active substance.

The hollow tubes used according to the invention may be made by means of the following techniques:
a) coextrusion of the two polymers in the melt,
b) melt extrusion of one of the two polymers followed by dipcoating with a solution of the other polymeric material from a suitable solution,
c) successive dipcoating with two solutions of the polymers.

To a). In case of coextrusion two molten polymeric materials are simultaneously pressed through an injection moulding nozzle via separated feeding systems. This injection moulding nozzle consists of two or more composed ducts or openings. The interior of the inner duct is a hollow needle through which inert gas can be injected via a separated feeding system. By selecting such a suitable construction of the injection moulding nozzle, hollow tubes can be formed having compact walls. The wall is made of a composition of the different polymeric materials. FIGS. 1a and b, 2 and 3a and b schematically show examples of the structure of the cross-section of different types of hollow tubes.

BRIEF DESCRIPTION OF THE DRAWINGS

FIGS. 1a and b show how a polymeric layer poorly permeable to the active substance partially covers the interior or the exterior of the highly permeable layer. By varying the surface coated with poorly permeable polymer the rate of delivery of the active substance can be adjusted.

Figure 2:
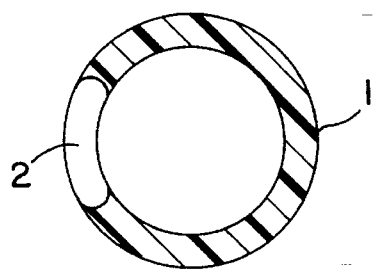
FIG. 2 shows a cross-section of a hollow tube of a polymer impermeable or poorly permeable to the active substance.

FIG. 2 schematically shows another cross-section of a hollow tube of a polymer substantially impermeable or poorly permeable to the active substance, in which a portion of the wall is replaced by a polymer permeable to the active substance. By varying the surface ratio of permeable/poorly permeable polymer the rate of delivery can be adjusted.

Figure 3A:
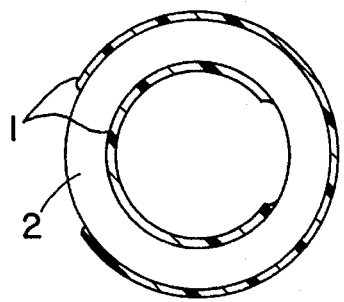
FIGS. 3a and 3b show a cross-section of a hollow tube having a wall consisting of a composition of more than two layers permeable and poorly permeable to the active substance.
Figure 3B:
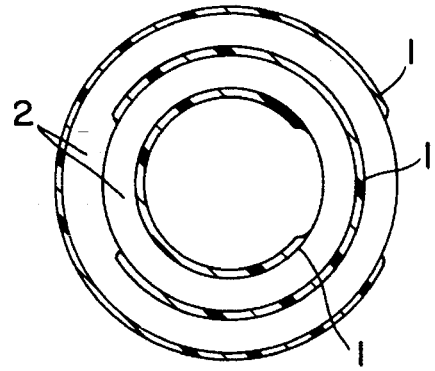

FIGS. 3a, b finally show a schematic cross-section of a hollow tube having a wall consisting of a composition of more than two layers permeable and poorly permeable to the active substance. By thus forming the structure of the wall of the hollow tube not only the available surface through which delivery of the active substance may occur, but also the distance over which the active substance must diffuse through the permeable layer is considerable extended. This may provide an additional possibility of controlling the level of delivery of the active substance.

To b). In case of melt extrusion followed by dipcoating a hollow tube having the desired wall structure is made in a multistage process. In stage 1 a hollow tube is made of permeable polymer by means of melt extrusion. In stage 2 the hollow tube is passed through a solution of poorly permeable polymer in a suitable solvent. By evaporation of the solvent under the proper conditions a hollow tube is formed having at its exterior a compact layer of poorly permeable polymer. Stage 2 can be repeated some times, if required. Finally, in stage 3 a portion of the outer layer is removed (e.g., cutting or perforating) to such an extent as to obtain the desired level of delivery of active substance (schematic cross-section shown in FIG. 1a). If required, prior to carrying out stage 2, the hollow tube made in stage 1 can be partially covered, followed by removing this cover after carrying out stage 2. Thus an article having the same structure will be obtained.

It is also possible to obtain a hollow tube having several permeable and poorly permeable layers by applying further dipping, drying and cutting procedures after stage 3.

To c). Both the compact permeable layer(s) and the poorly permeable layer(s) are made by means of the dipcoating technique described. By a proper combination of dipping, drying and cutting procedures hollow tubes are obtainable having the structures shown in FIGS. 1a, b and 3a, b. When making hollow tubes by means of the dipcoating process, the hollow tube must be supported by a metal, glass or plastic rod.

The hollow tubes made in the following examples have been made by means of the techniques mentioned under a), b), and c).

The article for the controlled delivery of active substance according to the invention has the following advantages:
the rate of delivery of an active substance from the article is easily adjustable by means of the structure of the article, using two or more biodegradable polymeric materials;
if desired, depending on, e.g., the wishes regarding the level of delivery, the article is degradable in parts during the period of implantation or degradable only after the active substance has been delivered completely;

the article is suitable for the optimum delivery of various types of medicines and other compounds.

If the article according to the invention is intended for subdermal use, it can be readily made via known per se techniques in a form in which the article can be easily applied subdermally by means of injection so that a surgery is superfluous and can be easily removed if it turns out that the patient does not endure the medicine.

Further to the above, it may be observed that the rate of delivery of the active substance is also adjustable by affecting the difference in permeability to the active substance within the employed combination of the at least two polymeric materials by adjustment of the pore structure of the polymeric materials in the article.

With reference to the accompanying drawing, which shows a number of tubular structures of the article, the invention can be further illustrated by the following examples. In the examples the delivery properties of hollow tubes are determined by using the steroid norgestrel. The values given in the following examples for the delivery of norgestrel were measured as follows:

The hollow tubes were cut to lengths of 4 cm and filled with a 30 wt. % dispersion of norgestrel castor oil. The ends of the filled tubes were sealed with acrylate glue impermeable to the hormone and then placed in glass vessels filled with 250 ml distilled water. Delivery experiments were carried out at 37° C. with continuous stirring (150 rpm) for a period of 6 months. The delivery of the norgestrel was measured spectrophotometrically at an absorption maximum of 247 nm.

The materials used for composing the hollow tubes were the polymer poly-L-lactic acid poorly permeable to norgestrel and the permeable polymer poly-ε-caprolactone, which materials are shown in the drawing by 1 and 2, respectively.

EXAMPLE I

Preparation of Article

Figure 1B:
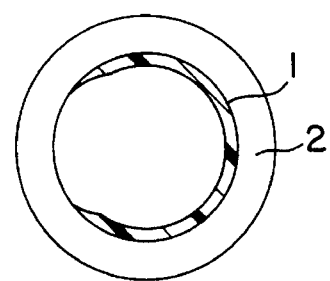

By coextrusion of poly-ε-caprolactone (Mv 50,000) at 70° C. and poly-L-lactic acid (Mv 180,000) at 190° C. a hollow tube was made having an external diameter of 1.5 mm and a total wall thickness of 180 µm. During extrusion a dry nitrogen atmosphere was maintained in the extruder. The poly-L-lactic acid covered 4/5 of the inner wall of the hollow tube consisting substantially of poly-ε-caprolactone (a schematic cross-section is shown in FIG. 1b). The layer thickness of the poly-L-lactic acid was 20 µm. Likewise made by extrusion were hollow tubes of poly-ε-caprolactone without a poly-L-lactic acid coating and hollow tubes internally covered completely with poly-L-lactic acid.

| DELIVERY OF NORGESTREL FROM THE HOLLOW TUBES MADE | | | |
|---|---|---|---|
| | hollow tube uncoated | hollow tube compl. coated | hollow tube 4/5 coated |
| delivery (µg/cm tube.day) | 21.5 ± 2.0 | 0.1 ± 0.03 | 4.8 ± 0.5 |

EXAMPLE II

Preparation of Article

Poly-ε-caprolactone (Mv 50,000) was extruded at 70° C. to form a tube having an external diameter of 1.5 mm and a wall thickness of 140 µm. By means of dipping into a 5 wt. % polymer solution of poly-L-lactic acid (Mv 130,000) in dioxane and subsequent evaporation of the solvent, samples having a length of 40 mm were provided exteriorly at room temperature with a poly-L-lactic acid coating having a thickness of 20 µm. Then 1/5 of the poly-L-lactic acid coating was removed by cutting (a schematic cross-section is shown in FIG. 1a). For the delivery tests there were also made a hollow tube of poly-ε-caprolactone uncoated with poly-L-lactic acid and a hollow tube of poly-ε-caprolactone completely coated with poly-L-lactic acid. Solvent residues were removed by an extensive flushing and drying procedure.

| DELIVERY OF NORGESTREL FROM THE HOLLOW TUBES MADE | | | |
|---|---|---|---|
| | hollow tube uncoated | hollow tube compl. coated | hollow tube 4/5 coated |
| delivery (µg/cm tube.day) | 23.0 ± 3.1 | 0.05 ± 0.01 | 5.0 ± 0.6 |

EXAMPLE III

Preparation of Article

A Teflon rod having a diameter of 1 mm was dipped at room temperature into a 10 wt. % polymer solution of poly-L-lactic acid (Mv 50,000) in dioxane. After evaporation of the solvent, 1/4 of the polymeric layer was removed, followed by dipping into 10 wt. % solution of poly-ε-caprolactone (Mv 50,000) in dioxane. After evaporation the rod was dipped once more into the solution of poly-L-lactic acid in dioxane. After evaporation, 1/4 was again removed from the exterior layer of poly-L-lactic acid. FIG. 3a shows a schematic cross-section of the hollow tube after removal from the Teflon rod. The thickness of the different layers was about 30 µm. The outside diameter of the hollow tube was 1.1 mm. Similarly, a hollow tube was made without a third layer of poly-L-lactic acid. Solvent residues were removed by an extensive flushing and drying procedure.

| DELIVERY OF NORGESTRAL FROM THE HOLLOW TUBES MADE | | |
|---|---|---|
| | 2-layered article | 3-layered article |
| delivery (µg/cm tube.day) | 31.5 ± 4.2 | 1.5 ± 0.03 |

FIG. 2 shows a tubular structure in which the wall portion 1 formed from relatively poorly permeable polymeric material and the wall portion 2 formed from relatively permeable polymeric material are composed to form a one-layered wall. A wall of this type is also made by forming the wall completely from the relative permeable material having distributed therein fewer or more large particles from the relatively poorly permeable polymer.

The difference in permeability to the active substance of the at least two polymeric materials of which the wall of the article is to be made may vary within very broad limits and is determined by the final object in conjunction with the nature of the active substance(s) for controlled delivery.

We claim:

1. An article for the controlled delivery of an active substance, comprising a hollow space fully enclosed by a wall and filled in full or in part with one or more active substances, wherein the wall is comprised of a portion or portions of a first polymeric material that is permeable to the active substance and is degradable and a portion or portions of a second polymeric material that is poorly permeable to the active substance relative to the first polymeric material and is degradable, and wherein there is a transport path for the delivery of the active substance from the hollow space to the surroundings of the article which is a continuous distance leading through the first polymeric material permeable to the active substance, and wherein the first and second polymeric materials are selected from polyesters, polyorthoesters, poly($\alpha$-amino acids), polydepsipeptides, polyanhydrides and polyphosphazenes, co- or block co-polymers derived therefrom and stereo complexes of polymers formed from optically active monomers of these biodegradable polymers.

2. An article as claimed in claim 1, wherein it is geometrically based on a hollow tube formed from the two polymeric materials in which the first polymeric material permeable to the active substance and the second poorly permeable polymeric material are each individually formed into a wall portion, which wall portions are assembled into a wall in the form of a two-layered laminate.

3. An article as claimed in claim 2, wherein the first polymeric material permeable to the active substance and the second poorly permeable polymeric material are composed to form the wall of the article which wall comprises a laminate of more than two layers.

4. An article as claimed in claim 2, wherein the individual wall sections of the first polymeric material permeable to the active substance and the second material poorly permeable to the active substance are assembled to form a one-layered wall.

5. An article as claimed in claim 1, wherein the active substances are selected from the group consisting of pharmaceuticals, hormones and peptides.

6. An article as claimed in claim 1, wherein the active substances are selected from the group consisting of cytostatics, pharmaceuticals, hormones and peptides.

7. An article as claimed in claim 3, wherein the active substances are selected from the group consisting of hormones, pharmaceuticals and peptides.

8. An article as claimed in claim 4, wherein the active substances are selected from the group consisting of peptides, pharmaceuticals and hormones.

9. An article as claimed in claim 1, wherein the active substances are selected from the group consisting of insecticides, herbicides, pheromones and repellents.

10. An article as claimed in claim 2, wherein the outside diameter of the hollow tube is not more than 5 mm and the length is not more than 10 cm.

11. An article as claimed in claim 10, wherein for human application the outside diameter of the hollow tube is 1.8 mm and the length is 4 cm.

12. An article as claimed in claim 1, wherein the permeability of the article to the active substance is effectuated by adjustment of the mutual relative permeability of the polymeric materials.

13. An article as claimed in claim 1, wherein the active substances are selected from the group consisting of insecticides, herbicides, pheromones and repellents.

14. An article as claimed in claim 3, wherein the outside diameter of the hollow tube is not more than 5 mm and the length is not more than 10 cm.

15. An article as claimed in claim 4, characterized in that the outside diameter of the hollow tube is not more than 5 mm and the length is not more than 10 cm.

16. An article as claimed in claim 10, characterized in that for veterinary application the outside diameter of the hollow tube is 3 mm and the length is 5 cm.

17. An article as claimed in claim 3, characterized in that the difference in permeability to the active substance is affectable within the employed combination of at least two polymeric materials by adjustment of the mutual relative porosity of the at least two polymeric materials.

18. An article as claimed in claim 4, characterized in that the difference in permeability to the active substance is affectable within the employed combination of at least two polymeric materials by adjustment of the mutual relative porosity of the at least two polymeric materials.

19. The article of claim 1, wherein the first and second polymeric materials are selected from the group consisting of the biodegradable copolymers consisting of polylactic acid, polyglycolic acid, poly(hydroxyvalerate), poly($\beta$-hydroxybutyric acid), poly($\epsilon$-caprolactone), poly($\alpha$-amino acids) and copolymers derived therefrom.

* * * * *